Oct. 19, 1971 D. L. ARMSTRONG Plant Pat. 3,077
ROSE PLANT
Filed Jan. 6, 1970
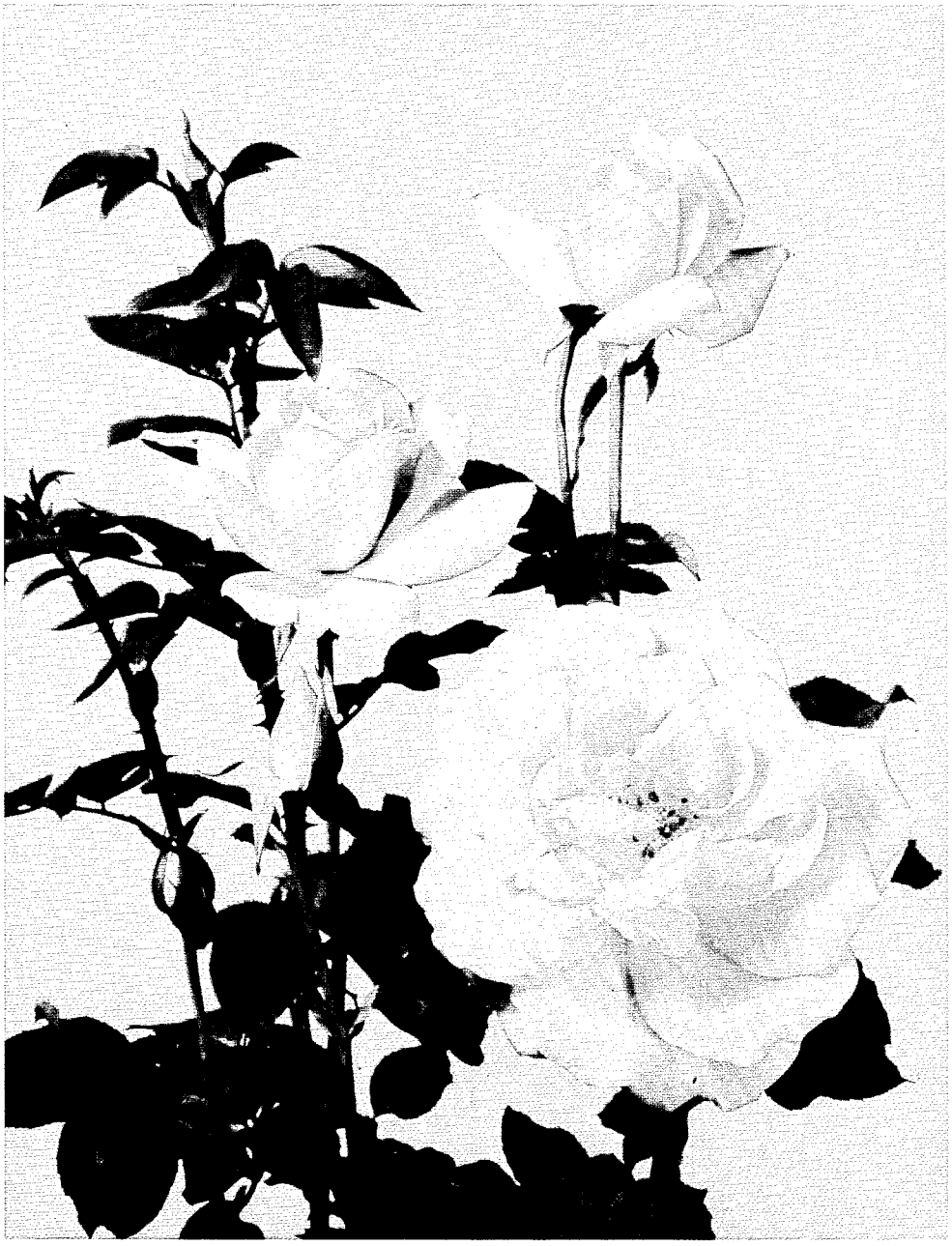

United States Patent Office

Plant Pat. 3,077
Patented Oct. 19, 1971

3,077

ROSE PLANT

David L. Armstrong, Upland, Calif., assignor to Armstrong Nurseries, Inc., Ontario, Calif.

Filed Jan. 6, 1970, Ser. No. 1,067
Int. Cl. A01h 5/00
U.S. Cl. Plt.—18 1 Claim

ABSTRACT OF THE DISCLOSURE

A bush rose plant of the hybrid tea class which is tall growing and adapted for outdoor cultivation. It is a free-growing, upright-spreading bush, much branched, producing large blooms of double petalage, which are generally purplish pink in overall color effect. The blooms are borne in abundance, almost continuously during the growing season, on straight, sturdy stems.

This invention relates to a new variety of bush rose plant of the hybrid tea class. The plant is tall growing in habit and is well adapted for outdoor cultivation, both for cut flowers and for garden decoration.

The plant is a seedling, bred by crossing Helen Traubel (P.P. 1,028) as the seed parent and Tiffany (P.P. 1,304) as the pollen parent. It holds its distinguishing characteristics through succeeding propagations by budding. It was originally propagated in Ontario, Calif.

The new variety is distinguished from its seed parent, Helen Traubel, in that the flower bud of the new variety is of medium length and ovoid in shape, whereas the flower bud of Helen Traubel is long and pointed. Whereas the overall color effect of Helen Traubel may be described as Apricot Pink, the new variety is Purplish Pink in effect. The new variety has a heavy and erect peduncle, which holds the flowers upright on the stems at all times, whereas the peduncle of the Helen Traubel variety is occassionally weak. Whereas the plant of Helen Traubel is moderately well branched and with a habit appropriately described as upright-spreading, the new variety is both more densely branched and the upright-spreading habit is substantially more upright than the habit of Helen Traubel. The older foliage of the new variety is light green in color, as compared with the dark green older foliage of the Helen Traubel plant.

This new variety is distinguished from its pollen parent, Tiffany, in the following ways. The new variety has fewer petals in the flower, ranging from 20 to 25, as compared to 25 to 30 in Tiffany. Tiffany is highly fragrant, whereas the new variety has a very subdued fragrance. Whereas the general color effect of Tiffany is Phlox Pink, the new variety is Purplish Pink. The color of the older foliage of this variety is consistently lighter green than is the foliage of Tiffany. Whereas the growth habit of Tiffany is characterized as upright, the new variety is much more branched and spreading.

In other words, the new variety has a branching habit of growth which differs from both of its parents, and the bloom has a purplish pink color which differs from the pink colors of either of its parents. Furthermore, the older foliage of the new variety is light green, as compared to the darker green of both parents.

The flowers of the new variety are usually borne singly, but occasionally in irregular clusters of 3 or 4, on strong long stems. The quantity of bloom is abundant and is merely continuous during the growing season under outdoor cultivation.

The accompanying drawing illustrates the plant in color, and shows the flowering thereof, from bud to full bloom.

In the description which follows, the color values stated conform to the Nickerson Color Fan.

*Bud*

The peduncle is of average length and average to heavy caliper, erect and smooth, with few, if any, stipitate glands and few, if any, small prickles. The color is near Light Olive, 10Y5/5, overlaid with near Moderate Yellowish Brown 10YR4/4, on the side exposed to the sun.

Before the calyx breaks, the bud is of medium size, medium length, and ovoid in form.

As the calyx breaks, the color is between Strong Red, 2.5R5/12, and Strong Purplish Red, 10RP4/12.

The inner surface of the sepals carries a fine, wooly tomentum, which lines the margins of alternate sepals, the margins of the intervening sepals having few, if any, small stipitate glands and small slender foliaceous appendages extending for about ¼ to ⅓ of the length of the sepal. The outer surface of the sepals is usually smooth.

As the first petal opens, the bud is of average size, medium length, usually urn-shaped to ovoid in form. The outside color is between Strong Purplish Pink, 7.5RP7/10, and Deep Pink, 10RP6/12. The small area at the base of the petal is near Brilliant Greenish Yellow, 7.5Y9/8. The inner color of the petal is between Strong Purplish Pink, 7.5RP7/10, and Strong Pink, 10RP7/8, the small area at the base of the petal being near Brilliant Yellow, 5Y9/9. The bud opens up well, and is not retarded or prevented from opening by cold, hot, wet, or drv weather.

*Bloom*

The bloom, when fully open, is large, ranging from 4½" to 5½". The petalage is double, showing from 20 to 25 petals, plus 4 to 6 petaloids, regularly arranged. In form the bloom is high centered at first, becoming cupped to high centered later on. The petals are cupped, tightly at first, more loosely at maturity. Outside and intermediate petals are reflexed only slightly outward along the apex in the newly-opened flower, but after being open for three days, these petals are usually reflexed slightly outward along the edges as well.

*Petals:*

The petals are of thick leathery texture, and are satiny in effect both inside and outside. The outside petals are between round and broadly obovate in form, with apex flat and usually with one to two notches. The intermediate petals are broadly obovate, with apex rounded and sometimes with one to two notches. The inside petals are likewise broadly obovate, with rounded apex and also sometimes with one to two notches. The colors may be modified by being shaded and/or washed with other colors.

The following description relating to a newly-opened flower was made from a rose grown outdoors in the month of September, in Ontario, Calif.

The color of the outside surface of the outer petal is between Strong Purplish Pink, 5RP7/9 and Strong Purplish Pink, 7.5RP7/10. The small area at the base of the petal is near Brilliant Greenish Yellow, 7.5Y9/8. The coloration of the inside surface of the outer petals is the same as that of the outside surface, except that the small area at the base of the petal is near Brilliant Yellow, 5Y9/9.

The outer surface of the intermediate petals is between Strong Purplish Pink, 7.5RP7/10, and Strong Pink, 10RP7/8. The small area at the base of the petal is near Brilliant Greenish Yellow, 7.5Y9/8. The inside surface of the intermediate petal is between Strong Purplish Pink, 5RP7/9, and Deep Purplish Pink, 7.5RP6/12, the small area at the base of the petal is near Brilliant Yellow, 5Y9/9.

The outer surface of the inner petals is near Strong Purplish Pink, 5RP7/9, the small area at the base of the petal being near Brilliant Yellow, 5Y9/9. The inner surface of the inner petals is between Strong Purplish Pink, 5RP7/9, and Deep Purplish Pink, 7.5RP6/12. The small area at the base of the petal is near Brilliant Yellow, 5Y9/9.

The following description was made from a rose that had been open for three days, having been grown outdoors during the month of September, in Ontario, Calif.

The color of the petals was almost uniform as between the outer surface and the inner surface of the outside petals, and this same coloration characterized the color of the inner and outer surfaces of the inside petals. It lay between Moderate Purplish Pink, 2.5RP7/8, and Strong Purplish Pink, 5RP7/9, the small area at the base of the petal being, in each instance, near Brilliant Greenish Yellow, 7.5Y9/8.

The general color effect of the newly-opened flower was between Strong Purplish Pink, 5RP7/9, and Deep Purplish Pink, 7.5RP6/12. The flower, after having been open for three days, displayed a general color effect between Moderate Purplish Pink, 2.5RP7/8, and Strong Purplish Pink, 5RP7/9.

The blooms drop off cleanly, and are not particularly affected by cold, hot, wet, or dry weather.

On the bush in the garden, the flowers persist for from 4 to 5 days in the month of September. Cut roses grown outdoors and kept at livingroom temperatures will last from 3 to 4 days in September.

*Reproductive organs*

Stamens: Average in number, arranged regularly about the pistils, a few mixed with petaloids.

Filaments: Medium length (5 to 10 mm.), near Vivid Yellow, 5Y8/12, in color, most of them with anthers.

Anthers: Small to medium in size, all open at about the same time, color both on the upper side and under side displaying margins near Strong Orange Yellow, 10YR7/10, with the remainder near Brilliant Yellow, 5Y9/9.

Pollen: Abundant, near Strong Orange Yellow, 7.5YR7/11, in color.

Pistils: Average in number, approximately 80.

Styles: Uneven, of average length, thin in caliper, and bunched. The upper third of the styles is near Strong Purplish Pink, 7.5RP7/10; the remainder is near Brilliant Greenish Yellow, 7.5Y9/8.

Stigma: Near Pale Orange Yellow, 7.5YR9/4, in color.

Ovaries: Usually all enclosed in the calyx.

Hips: Average length, between obovoid and globular in shape, their color at maturity being between Moderate Brown, 7.5YR4/5, and Moderate Yellowish Brown, 10YR4/4. They are rough, with thick fleshy walls.

Sepals: Medium length and straight, falling soon. The inside color is near Moderate Olive Brown, 2.5Y4/4. The color outside is near Moderate Yellowish Brown, 10YR4/4.

Seeds: Few to average in number, small to medium size, ranging usually from 15 to 20.

*Foliage*

The foliage consists of compound leaves comprising usually 3 to 7 leaflets. These are usually abundant, and of medium to large size. They are leathery in texture and semi-glossy in effect.

The shape of the leaflets is generally oval, with acute apex and round base. The margin is doubly serrate.

The color of the mature leaf on the upper surface is between Moderate Olive Green, 5GY4/3, and Grayish Olive Green, 5GY3/2. On the under surface, it is near Moderate Olive Green, 7.5GY4/4.

The younger foliage on its upper surface is near Moderate Olive Green, 5GY4/3, the under surface being near Moderate Yellow Green, 5GY5/6, with veins near Deep Purplish Red, 7.5RP3/9.

The rachis is of average to heavy size, with its upper side grooved and with few to several small stipitate glands on the edges. The under side of the rachis is smooth, but with a few stipitate glands and occasional small prickles.

The stipules are of medium length and medium width, with short points, turning out at an angle of less than 45°.

The plant is more resistant than average to mildew, as compared with other varieties grown commercially under comparable conditions, in Ontario, Calif.

*Growth*

The plant is characterized by very free growth, being upright-spreading, and much branched in habit. Its canes are medium to heavy caliper.

The main stems are near Moderate Olive Green, 2.5GY4/3. Their large prickles are numerous, of short to medium length, almost straight, with short base, and near Brownish Orange, 5YR5/8, in color. The small prickles are few in number and their color is likewise near Brownish Orange, 5YR5/8. There are no hairs.

The branches are between Moderate Olive Green, 5GY4/3, and Moderate Yellow Green. 5GY5/6. Their large prickles are from few to several in number, hooked slightly downward, and with short bases. Their color is near Moderate Reddish Brown, 2.5YR3/3. There are no hairs.

The color of the new shoots is near Moderate Yellow Green, 2.5GY5/5, overlaid with near Moderate Reddish Brown, 10R3/4, on the side exposed to the sun. There are several large prickles on the new shoots, of short to medium length, hooked slightly downward and with short base. These are near Moderate Reddish Brown, 7.5R3/6. There are a few small prickles which are also near Moderate Reddish Brown, 7.5R3/6, but no hairs.

I claim:

1. A bush rose of the hybrid tea class, substantially as herein shown and described, the same being distinguished by a novel combination of features including the free, upright-spreading habit of growth of the plant, which has sturdy canes and carries its flowers on strong straight stems, supported by nearly smooth peduncles, the plant as a whole having a resistance to mildew which is above average for roses of the same class under parallel conditions of cultivation; and the transition in flowering from a strong red-purple bud to a deep pink open flower, tight-cupped at first but loosely cupped at maturity, and with satin textured double petalage.

No references cited.

ROBERT E. BAGWILL, Primary Examiner